US008990054B1

(12) United States Patent
Ketterling et al.

(10) Patent No.: US 8,990,054 B1
(45) Date of Patent: Mar. 24, 2015

(54) SYSTEM AND METHOD FOR DETERMINING AND TRAINING A PEAK PERFORMANCE STATE

(76) Inventors: Debra C. Ketterling, Mesa, AZ (US); Kanav Kahol, New Delhi (IN)

(*) Notice: Subject to any disclaimer, the term of this patent is extended or adjusted under 35 U.S.C. 154(b) by 392 days.

(21) Appl. No.: 13/410,838

(22) Filed: Mar. 2, 2012

Related U.S. Application Data

(60) Provisional application No. 61/448,979, filed on Mar. 3, 2011.

(51) Int. Cl.

| | |
|---|---|
| ***A61B 5/0482*** | (2006.01) |
| ***A61B 5/00*** | (2006.01) |
| ***A63B 69/00*** | (2006.01) |
| *A63B 69/36* | (2006.01) |
| *G09B 19/00* | (2006.01) |
| *G06F 19/00* | (2011.01) |

(52) U.S. Cl.
CPC ............. *A61B 5/486* (2013.01); *A63B 2230/10* (2013.01); *A61B 5/7267* (2013.01); *G09B 19/0038* (2013.01); *A63B 69/3608* (2013.01); *A63B 69/00* (2013.01); *G06F 19/3431* (2013.01)
USPC ................ 703/2; 600/301; 600/545; 434/247

(58) Field of Classification Search
None
See application file for complete search history.

(56) References Cited

U.S. PATENT DOCUMENTS 3,821,949 A 7/1974 Hartzell et al. ................ 128/2.1
4,949,726 A 8/1990 Hartzell et al. ............... 128/731
5,450,855 A 9/1995 Rosenfeld ..................... 128/732
5,694,939 A 12/1997 Cowings ....................... 128/671
5,697,791 A * 12/1997 Nashner et al. ............... 434/247
5,899,867 A * 5/1999 Collura ......................... 600/545
6,032,530 A * 3/2000 Hock ............................ 600/595
7,117,032 B2 10/2006 Childre et al. ................ 600/545
7,163,512 B1 1/2007 Childre et al. ................ 600/500
7,269,456 B2 9/2007 Collura ......................... 600/545
7,331,870 B2 2/2008 Smith et al. ...................... 463/36
7,460,903 B2 12/2008 Pineda et al. ................. 600/544
7,713,212 B2 5/2010 Elliott .......................... 600/500
7,919,945 B2 4/2011 Houston et al. ............... 318/460
8,066,637 B2 11/2011 Childre et al. ................ 600/300
8,388,530 B2 * 3/2013 Shusterman .................. 600/300
8,500,604 B2 * 8/2013 Srinivasan et al. ............ 434/247
8,655,817 B2 * 2/2014 Hasey et al. ..................... 706/45
8,702,430 B2 * 4/2014 Dibenedetto et al. ......... 434/247

(Continued)

OTHER PUBLICATIONS

Seventeen (17) page article entitled "Algorithms for Manifold Learning" by Lawrence Cayton; dated Jun. 14, 2005.

(Continued)

*Primary Examiner* — Aniss Chad
*Assistant Examiner* — Jay B Hann
(74) *Attorney, Agent, or Firm* — Blake P. Hurt

(57) ABSTRACT

A system and method for determining a peak performance state by coherency of input signals from a test subject. The system includes two sensors for receiving separate input signals from a test subject. The system also includes a processor that is in communication with the sensors. The system further includes a memory that stores baseline data and is connected to the processor. The method includes the steps of receiving input signals from two sensors, communicating the input signals to a processor, analyzing the input signals with the processor as a function of a nonlinear relationship to determine coherency, and comparing the coherency data to baseline data stored in the memory to determine the presence of a peak performance state.

19 Claims, 3 Drawing Sheets

(56) References Cited

U.S. PATENT DOCUMENTS

| | | | | |
|---|---|---|---|---|
| 2005/0240114 | A1 | 10/2005 | Elliott | 600/520 |
| 2006/0057549 | A1* | 3/2006 | Prinzel et al. | 434/247 |
| 2006/0281543 | A1 | 12/2006 | Sutton et al. | 463/29 |
| 2007/0185533 | A1 | 8/2007 | Gerdes | 607/1 |
| 2007/0270668 | A1 | 11/2007 | Childre et al. | 600/300 |
| 2008/0082020 | A1 | 4/2008 | Collura | 600/545 |
| 2008/0177197 | A1 | 7/2008 | Lee et al. | 600/545 |
| 2008/0214903 | A1* | 9/2008 | Orbach | 600/301 |
| 2009/0005837 | A1 | 1/2009 | Olmstead | 607/88 |
| 2009/0069707 | A1 | 3/2009 | Sandford | 600/545 |
| 2009/0099474 | A1 | 4/2009 | Pineda et al. | 600/545 |
| 2009/0118636 | A1 | 5/2009 | Collura | 600/545 |
| 2009/0124920 | A1 | 5/2009 | Patterson et al. | 600/544 |
| 2009/0221928 | A1 | 9/2009 | Einav et al. | 600/544 |
| 2009/0281400 | A1 | 11/2009 | McCraty et al. | 600/301 |
| 2009/0281447 | A1 | 11/2009 | Gerdes | 600/544 |
| 2009/0312663 | A1 | 12/2009 | John et al. | 600/544 |
| 2009/0318826 | A1 | 12/2009 | Green et al. | 600/545 |
| 2010/0094156 | A1 | 4/2010 | Collura | 600/545 |
| 2010/0106043 | A1 | 4/2010 | Robinson et al. | 600/544 |
| 2011/0054359 | A1* | 3/2011 | Sazonov et al. | 600/595 |
| 2011/0105859 | A1* | 5/2011 | Popovic et al. | 600/301 |

OTHER PUBLICATIONS

Six (6) page article entitled: “Haptic System to Alert Users Before Impending Human Errors”; by Kanav Kahol and Foad Saeidi; from *Haptic Audio Visual Environments and Games*; issued Nov. 7-8, 2009.

Four (4) page article entitled: “How to Train Your Brain”, by Guy Yocom; from *Golf Digest*; dated Oct. 2010.

* cited by examiner

SYSTEM AND METHOD FOR DETERMINING AND TRAINING A PEAK PERFORMANCE STATE

This non-provisional patent application claims all benefits under 35 U.S.C. §119(e) of U.S. provisional patent application Ser. No. 61/448,979, entitled "SYSTEM AND METHOD FOR COHERENCE BASED ANALYSIS AND FEEDBACK", filed 3 Mar. 2011 in the United States Patent and Trademark Office, which is incorporated by reference in its entirety herein.

FIELD OF THE INVENTION

The invention herein pertains to a system and method for determining a peak performance state in a test subject and particularly pertains to utilizing nonlinear analysis of input signals collected from a test subject to determine coherency therein.

DESCRIPTION OF THE PRIOR ART AND OBJECTIVES OF THE INVENTION

The human biological system is associated with a number of physiological functions such as cognition, respiration and motion. When accomplishing these physiological functions, the body generates electrical signals referred to herein as "input signals". Examples of physiological input signals include electrical activity of muscle that is detected, measured, and recorded by an electromyogram (EMG), an electrocardiogram (ECG), or electrical activity that is associated with mental activity which is measured and recorded by an electroencephalogram (EEG). Examples of non-physiological input signals include detection and measurement of time, acceleration, velocity and displacement as a type of movement.

It is well known in the field of performance psychology that peak performance of a task results from the presence of a physiological state comprising one or more optimal measured values of physiological and non-physiological input signals. Putting a golf ball, shooting a basketball, or throwing darts are all examples of activities whose successful completion have been linked with the presence of a peak performance state concurrent with the physical performance of the activity. The presence of such an optimal physiological state in athletics is colloquially referred to as "being in the zone".

Physiological states can be measured and classified by available algorithms that monitor physiological and non-physiological signals and mathematically determine the associated physiological coherent state. Typically, an optimal physiological state for task performance deemed present if all of the measured values of physiological and non-physiological signals defining the physiological state are equal to the values measured when a task is performed successfully within a defined frequency and duration, for example, sinking a golf putt nine times out of ten. This traditional approach tends to model a performance state as a function of separate changes in physiological and non-physiological signals and seeks to ascertain a predefined threshold of the signals to compare defined optimal states to the current states. This is a linear comparison, in that it defines the relationship between the physiological and non-physiological signals as measured and the presence of a peak performance state as a direct comparison between the recorded and expected values. This approach is rarely accurate in ascertaining the presence of a peak performance state as the underlying physiological and non-physiological signals are complex and dynamic. Further, comparing physiological and non-physiological data to standardized values is often limited in ascertaining and describing the optimal performance state in a given test subject.

It is therefore preferable to model peak performance states as a function of coherence between physiological and non-physiological signals. For example, established approaches have sought to find mathematical coherence between different EEG channels to identify the similarity of activity in different regions of the brain and use the similarity as a measure of peak performance. Thus far, these approaches have had limited success due to the underlying mathematical techniques used to study region similarity because the signals have been limited to a pairwise comparison. This technique fails to accurately identify and characterize the optimal performance state of a given individual for the same reasons that a linear comparison fails.

One of ordinary skill in the art will also be aware that memory devices refer to any form of electronic memory including all forms of sequential, pseudo-random, and random access memory (RAM) storage devices. Storage devices as known within the current art include all forms of RAM, magnetic and optical tape, magnetic and optical disks, along with various other forms of solid-state mass storage devices. The disclosed invention applies to all forms and manners of memory devices including, but not limited to, storage devices utilizing magnetic, optical, and chemical techniques, or any combination thereof.

As referred to herein, the term "computer" should be broadly construed. For example, a computer may be any electronic device configured to present physiological and non-physiological data to a user. Examples of such a computer include, but are not limited to, conventional desktop computers as well as laptop computers. In another example, a computer may be a mobile device such as, for example, but not limited to, a smart phone, a cell phone, a pager, a personal digital assistant (PDA), a mobile computer with a smart phone client, or the like. A computer may also be a typical mobile device with a wireless data access-enabled device (e.g., an iPHONE® smart phone, a BLACKBERRY® smart phone, a NEXUS ONE™ smart phone, an iPAD® device, or the like) that is capable of sending and receiving data in a wireless manner using protocols like the Internet Protocol, or IP, and the wireless application protocol, WAP, or BLUETOOTH®. This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of mobile wireless devices. In one embodiment, the mobile device is a cellular telephone or smart phone that operates over GPRS (General Packet Radio Services), which is a data technology for GSM networks. In addition to a conventional voice communication, a given mobile device can communicate with another such device via many different types of message transfer techniques, including SMS (short message service), enhanced SMS (EMS), multi-media message (MMS), email WAP, paging, or other known or later-developed wireless data formats.

As referred to herein, a "user interface" is generally a system by which users interact with a computer. An interface can include an input for allowing users to manipulate a computer, and can include an output for allowing the system to present information (e.g., electronic text) and/or data, to indicate the effects of the user's manipulation, etc. An example of an interface on a computer includes a graphical user interface (GUI) that allows users to interact with programs in more ways than typing. A GUI typically can offer display objects, and visual indicators, as opposed to text-based interfaces, typed command labels or text navigation to represent information and actions available to a user. For example, an interface can be a display window or display object, which is selectable by a user of a mobile device for interaction. The display object can be displayed on a display screen of a computer and can be selected by, and interacted with by, a user using the interface. In an example, the display of the computer can be a touch screen, which can display the display icon. The user can depress the area of the display screen at which the display icon is displayed for selecting the display icon. In another example, the user can use any other suitable interface of a mobile device, such as a keypad, to select the display icon or display object. For example, the user can use a track ball or arrow keys for moving a cursor to highlight and select the display object.

Operating environments in which embodiments of the present disclosure may be implemented are also well-known. In a representative embodiment, a mobile computer such as a laptop is connectable (for example, via WAP) to a transmission functionality that varies depending on implementation. Thus, for example, where the operating environment is a wide area wireless network (e.g., a 2.5G network, a 3G network, or a 4G network), the transmission functionality comprises one or more components such as a mobile switching center (MSC) (an enhanced ISDN switch that is responsible for call handling of mobile subscribers), a visitor location register (VLR) (an intelligent database that stores on a temporary basis data required to handle calls set up or received by mobile devices registered with the VLR), a home location register (HLR) (an intelligent database responsible for management of each subscriber's records), one or more base stations (which provide radio coverage within a cell), a base station controller (BSC) (a switch that acts as a local concentrator of traffic and provides local switching to effect handover between base stations), and a packet control unit (PCU) (a device that separates data traffic coming from a mobile device). The HLR also controls certain services associated with incoming calls. Of course, embodiments in accordance with the present disclosure may be implemented in other and next-generation mobile networks and devices as well. The mobile device is the physical equipment used by the end user, typically a subscriber to the wireless network. Typically, a mobile device is a 2.5G-compliant device, 3G-compliant device, or 4G-compliant device that includes a subscriber identity module (SIM), which is a smart card that carries subscriber-specific information, mobile equipment (e.g., radio and associated signal processing devices), a user interface (or a man-machine interface (MMI)), and one or more interfaces to external devices (e.g., computers, PDAs, and the like). The computer may also include a memory or data store.

Special training techniques have been previously developed to allow test subjects to exert conscious control over physiological activities in order to achieve an optimal physiological state for peak performance. The technique of biofeedback is a process that enables a test subject to learn how to change physiological activity for the purpose of improving health and performance. Precise instruments measure physiological activities such as brain waves, heart function, breathing, muscle activity and skin temperature. These conventional instruments rapidly and accurately "feed back" information of the test subject. The presentation of this information, often in conjunction with changes in thinking, emotions, and behavior, supports desired physiological changes. Over time, these changes can endure without continued use of any instrument. The promise of techniques such as biofeedback for improved mental and physical control is tied to the identification and characterization of optimal physiological states for a test user, but the current approaches are lacking in accuracy as discussed above.

Thus, in view of the problems and disadvantages associated with prior peak performance state devices and methods for determination, the present invention was conceived and one of its objectives is to provide a system for determining the presence of a peak performance state of an individual during an activity.

It is another objective of the present invention to provide an apparatus that can quickly and accurately determine coherence of physiological and non-physiological input signals utilizing nonlinear mathematical techniques.

It is still another objective of the present invention to provide a device that can learn that which constitutes the peak physiological state of a test subject.

It is yet another objective of the present invention to provide a system that presents fast and accurate coherency information to a test subject for the purpose of feedback training.

It is a further objective of the present invention to provide an apparatus that responds to a given mental state of a test subject with audible sounds, visual text, or vibrations.

It is still a further objective of the present invention to provide a method for identifying and characterizing the optimal performance state of a test subject.

It is yet a further objective of the present invention to provide a method for calculating the coherency of physiological and non-physiological input signals to determine the presence or lack of an optimal performance state.

It is yet still a further objective of the present invention to provide a method for determining the peak performance state of an individual during an activity and to train the individual to perform the activity in the predetermined peak performance state.

Various other objectives and advantages of the present invention will become apparent to those skilled in the art as a more detailed description is set forth below.

SUMMARY OF THE INVENTION

The aforesaid and other objectives are realized by providing a system and method for determining a peak performance state of a test subject's coherency of input signals therefrom. The system includes two or more sensors for receiving separate physiological and non-physiological input signals from a test subject while performing an activity. The system also includes a processor that is in communication with the sensors. The system further includes a memory connected to the processor. The system also has an algorithm stored in the memory used for calculating coherency between input signals. The system further includes baseline data that is stored in the memory and is used to compare the coherency of input signals to determine a peak performance state of the test subject. The system further includes a feedback mechanism controlled by the algorithm for notifying the test subject of the current peak performance state. The system also has an additional external sensor for determining duration of a measurement window used to define the amount of time input signals are detected by the sensors.

Also disclosed is a method for determining a peak performance state of a test subject by coherency of input signals that includes receiving separate input signals from two or more sensors, communicating the signals to a processor, analyzing the input signals with the processor as a function of a nonlinear relationship to determine coherency, and comparing the coherency data to baseline data stored in the memory to determine the presence of a peak performance state and train the test subject to perform within their predetermined peak performance state.

DETAILED DESCRIPTION OF THE PREFERRED EMBODIMENT AND OPERATION OF THE INVENTION

The present invention involves a computerized method and apparatus for measuring peak performance in at least one test subject engaged in performance of a task by analyzing input signals and their coherence. Coherence in multiple signals can be identified substantially simultaneously and may involve conventional as well as unique systems and methods as a novel sequence of activity peaks and troughs. The apparatus and method disclosed herein allow measuring and training coherence at any level of activation.

One or more embodiments of this disclosure are intended to encompass a computerized system and method of feedback training for attaining an optimal physiological state consistent with the successful performance of a task by finding coherence between two or more input signals. It is to be understood that the computerized system and method disclosed may utilize conventional hardware now known such as, but not limited to, computers, processors, servers, memory devices, storage devices, transmitters, communication devices, and any other appropriate hardware that one of ordinary skill would recognize as appropriate for implementation.

The preferred embodiment of a system for determining a peak performance state of a test subject by coherency from input signals includes several sensors for receiving separate signals from the brain, heart, feet and golf club of a test subject. The preferred system also includes a processor in communication with the several sensors and connected to a memory device which stores an algorithm and baseline data used in determining input signals nonlinear coherency. The preferred algorithm for coherency calculation is a combination of a manifold learning algorithm and a support vector machine algorithm. The preferred system further includes a feedback unit carried by the test subject to alert a test subject through auditory and haptic outputs of the test subject's current physiological state.

The preferred method for determining a peak performance state of a test subject by coherency from input signals includes the steps of providing an apparatus, receiving separate input signals by sensors proximate the head, feet and heart of a user as well sensors placed on the object of use depending on the activity being performed such as for example a baseball bat, golf club or otherwise. Thereafter communicating input signals received from all of the sensors to the processor, analyzing the input signals by the processor with the algorithm as a function of their nonlinear relationship for determining coherency, comparing coherency to baseline data to determine peak performance state of a test subject, and providing a feedback mechanism for notifying the test subject of the current peak performance state.

Figure 1:
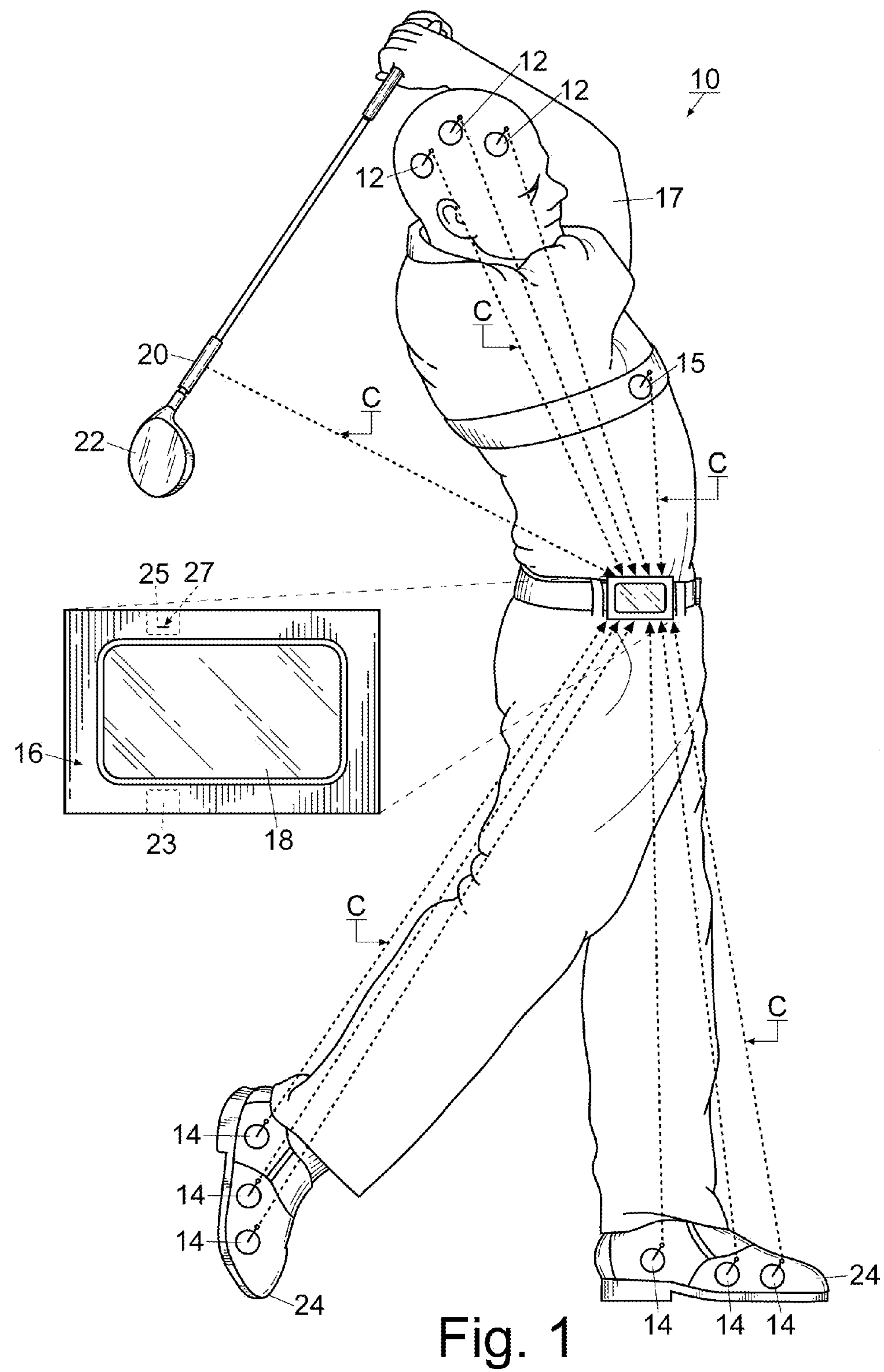
FIG. 1 is a schematic illustration of an apparatus for determining a peak performance state by coherency of input signals from a test subject disclosed herein.

For a better understanding of the invention and its method of operation, turning now to the drawings, FIG. 1 is a schematic illustration of apparatus 10 for determining a peak performance state by coherency of input signals 19 (see FIG. 2) from test subject 17. For the purpose of illustrating the disclosed apparatus, test subject 17 is shown as a golfer and is understood to be swinging golf club 22. However, the disclosed system could be used to train test subject 17 during performance of any activity, with examples ranging from shooting billiards, shooting a basketball or shooting a sniper rifle.

Apparatus 10 includes sensors 12, 14 and 15 and feedback unit 16 which carries feedback screen 18 as well as processor 23 and memory 25. Stored in memory 25 is an algorithm for calculating coherence between the incoming input signals 19 (FIG. 2) and baseline data 27 (shown schematically in FIG. 1) to compare to the coherency. As seen schematically in FIG. 1, sensors 12 are positioned on the head, sensors 14 are positioned on the shoes and sensor 15 is located near the heart. Sensors 12, 14 and 15 are conventional electrical sensors well-known in the art that are configured to capture physiological or non-physiological signals. Examples include electrical signals from the brain or heart of test subject 17 as well as non-electrical signals in the form of pressure data from shoes 24 on the feet of test subject 17 or temporal data from the swinging of golf club 22 by exterior sensor 20. Sensors 12, 14 and 15 may operate individually by attaching to test subject 17 proximate the sources of input signals 19 (FIG. 2), as shown by heart sensor 15 but a more accurate signal measurement is achieved by using sensors 12, 14 and 15 collectively. Although not shown, in one embodiment, the number of head sensors 12 totals fourteen separate sensors 12, however more or less sensors 12 could be utilized.

For example, FIG. 1 shows head sensors 12 and foot sensors clustered around their respective targets. In this embodiment, head sensors 12 operate similarly to a standard EEG and may be attached directly to the head of test subject 17. In the event that test subject 17 has hair (not shown), test subject 17 need only moisten the hair before attaching head sensors 12. Although separate head sensors 12 can function as a group, one or more embodiments of apparatus 10 may incorporate a plurality of head sensors 12 into a garment such as a hat or visor (not shown) to prevent head sensor 12 displacement and inaccurate readings from input signals 19. Further, sensors 12, 14 and 15 are shown communicating with feedback device 16 via radio frequency waves labeled "C" but sensors 12, 14 and 15 could also connect to feedback device 16 through other wireless or optical communication systems (not shown) in addition to conventional wire connections, although this is not preferable for obvious logistical reasons.

Sensors 14 are shown attached to shoes 24 on the feet of test subject 17, and may record weight shifting between the right foot and the left foot of test subject 17 as well as shifting between the front and back of each foot via frequency waves C from separate sensors 14. In an alternate embodiment, sensors 14 may be incorporated into a shoe insert or outer shoe attachment (not shown) to record weight shifting as a collective group.

Another example of a sensor in FIG. 1 is exterior sensor 20 which is carried on golf club 22. Exterior sensor 20 is configured to measure the amount of time sensors 12, 14 or 15 may monitor according to various physiological and non-physiological inputs received. The temporal function of exterior sensor 20 is vital to the determination of an optimal performance state and the calculation of coherency among input signals 19 collected from test subject 17. In one embodiment of apparatus 10, exterior sensor 20 may also be configured to provide speed and acceleration data of the golf swing of test subject 17 in addition to establishing the temporal duration of the measurement window.

FIG. 1 also presents an expanded illustration of feedback unit 16. In one embodiment, test subject 17 may carry feedback unit 16 on for example a belt around the waist, as shown in FIG. 1. Feedback unit 16 houses processor 23 as well as a memory device 25. Memory device 25 is known in the art as, for example a solid-state memory or traditional RAM. Stored in memory device 25 is an algorithm for analyzing input signals 19 (FIG. 2) as a function of a nonlinear relationship detected from sensors 12, 14 and 15 and determining coherency of input signals 19.

Multiple measurements of physiological and non-physiological signals result in a high dimensional data set. One of ordinary skill in the art will understand that dimensionality of data for the purpose of this disclosure can mean the number of distinct non-overlapping values gathered from input signals 19. For example, movement of a limb can be captured by six elements (translation in three directions and rotations around three directions). These six measurements result in six dimensions. Similarly, an EEG with fourteen channels has fourteen dimensions. Therefore, for an implementation of the present disclosure that includes both the EEG and movement of the limb, a total of twenty dimensions exist.

Modern data analysis tools are designed to work on high dimensional data whose components are not independently distributed. However, high dimensional spaces show surprisingly counter-intuitive geometrical properties that have a large influence on the performance of data analysis tools. This limits the application of traditional approaches to optimal physiological state detection. Direct linear or pairwise comparison of input signals 19 to a peak performance standard is neither entirely accurate nor suitable for providing feedback when multiple dimensions are detected from input signals 19.

One approach to address high dimensional data is to reduce the dimensionality. There are many approaches to dimensionality reduction based on a variety of assumptions and used in several contexts. In some instances, high dimensional data may be simpler than the dimensionality would indicate. Specifically, a given high dimensional data set may contain many features that are all measurements of the same underlying cause and are therefore closely related. For example, the physiological state of "challenge" in human physiology is associated with elevated EEG and ECG signals in addition to a corresponding increase in skin temperature. This intuition is formalized using the notion of a manifold: the data set lies along a low-dimensional manifold embedded in a high dimensional feature space. A nonlinear relationship may exist between low-dimensional manifold and high-dimensional feature representations. Manifold learning can provide the framework for analyzing nonlinear signal coherency. Therefore, use of a manifold learning algorithm is one embodiment of the present disclosure that efficiently projects high-dimensional data representing physiological and non-physiological input signals into low-dimensional data.

While a manifold may be obtained by linear techniques such as principal component analysis or linear discriminant analysis, these approaches are limited in high dimensionality situations both in terms of time and accuracy. As a nonlinear relationship may exist between a manifold and its high dimensional feature representation, it is preferable to obtain a manifold by nonlinear analysis techniques, for example the isomap approach, local linear embedding, laplacian eigenmaps, and semidefinite embedding. *Algorithms for Manifold Learning* by Lawrence Cayton (2005) gives a small representation of the algorithms that take high dimensional inputs and find their underlying manifold and is incorporated herein by reference.

Further, the manifolds in lower dimension space can be separated based on the expertise level or performance level of test subject 17. Turning to the golf example in FIG. 1, the manifold for a successful putt is different from the manifold of a missed putt, just as the manifold of an expert golfer differs from the manifold of a novice player. For a given input signal 19 being received, the algorithms for manifold learning project the high dimensional data point into lower dimensions. The closeness of the data point to manifolds for different classes reveals the identified class of the task as well as that of the test subject. The closeness can be defined by, for example, Euclidean distance, city block distance, or mahalanobis distance. It is this distance determination that is used as a comparison to the coherency of the multiple input signals 19 of apparatus 10 to define the presence of a peak performance state in test subject 17.

In addition to manifold learning, there are a category of sophisticated nonlinear algorithms that can aid in the expertise classification of test subject 17 in a given activity. The support vector machine algorithm is popular not only because of its rigorous formulation, but also because it is widely applicable in real-world problems resulting in improvement over traditional methods. Therefore, the integration of support vector machine with manifold learning can recognize the optimal state of coherence more efficiently and more accurately.

In another embodiment of apparatus 10, the memory also stores baseline data to compare to the coherency of input signals 19. The baseline data may take a number of forms but an initial threshold level constituting of an optimal physiological state or signal coherency may be predetermined for inaugural use of apparatus 10. Subsequently, state space model may be used to identify the dynamic quality of input signal 19 shift. For example, brain and limb activity follow a certain temporal pattern and this pattern can predict whether a successful or unsuccessful activity will occur at a given expertise level.

Figure 2:
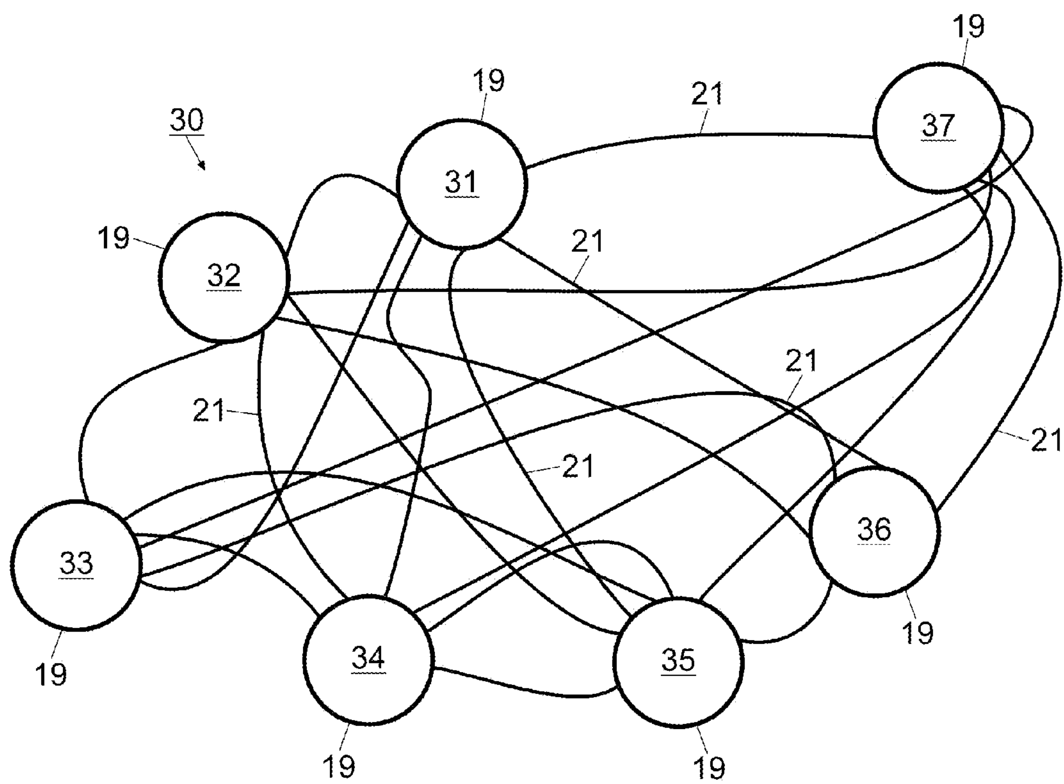
FIG. 2 demonstrates schematically a state transition model for optimal physiological state determination.

FIG. 2 demonstrates a schematic overview of state transition model 30 for optimal physiological state determination. Circles 31-37 represent input signals 19 and each connection or transition line 21 between circles 31-37 represents a transition from one physiological state to the next. Transition 21 occurs when a value of input signal 19 is observed within a given physiological state. Each state has a defined probability of being a beginning or initial state. State transition model 30 is designed so that each state corresponds to a single input signal 19. When a local maximum or minimum in all incoming input signals 19 occurs, it is labeled an event and model 30 transitions to the corresponding state. Over time, as further events occur the model transitions to different states depending on the occurrence of a new event. The notion of signal emphasis shifting from one state to another and then existing in a state and expressing a value of that event is augmented by a beginning state that is defined as incoming input signals 19 that first express an event at a certain time instant.

Model 30 as discussed above can be captured by a Hidden Markov Model (HMM). An HMM models a temporal sequence of events (referred to as an observation sequence) in terms of state machine, in which the current state of the model is probabilistically dependent on the previous states. HMMs have a finite number of probabilities and transitions between the states are governed by transition probabilities. In every state, an output symbol can be generated according to an associated probability distribution. Further, there is a probabilistic function that governs the beginning state in the state mode called the initial probability distribution. Only the observation symbols are available to an external viewer and the state generating the symbol is hidden.

Mathematically an HMM λ can be defined as:

$$\lambda=\{A,B,\Pi\} \quad (1)$$

where A refers to a set of transition probabilities such that $A=\{a_{ij}\}$ where $a_{ij}$ represents transitions from state i to state j, $$a_{(i,j)}=p\{q_{t+1}=j|q_t=i\},\ 1\le i,\ j\le N \quad (2)$$

where N is the number of states and $q_t$ denotes the current state. Transition probabilities satisfy the following constraints:

$$a_{ij}\ge 0,\ \Sigma_{i=1}^{N}a_{(ij)}=1, 1\le i,j\le N \quad (3)$$

where B is a set of probability distributions in each of the states $\{b_j(k)\}$ such that $b_j(k)$ represents the probability of generation of observation symbol k at state j, $$b_j(k)=p\{o_t=v_k|q_t=j\}\ 1\le t\le N,\ 1\le k\le M \quad (4)$$

where $v_k$ denotes the $k^{th}$ observation symbol in the sequence, $o_t$ is the current observation symbol and M is the number of total observation symbols.

The following stochastic constraints must be satisfied, where Π is the initial state distribution.

$$\Sigma_{k=1}bj(k)=1 \quad (5)$$

$$\Pi=p(q_1=i),\ 1\le i\le N \quad (6)$$

The parameters of HMM λ may be adjusted in order to maximize the probability of production of a given sequence O by a given HMM λ (denoted p(O|λ)) to overcome a problem in defining and learning HMMs known as the Learning Problem. The Maximum Likelihood criterion is used to maximize the likelihood of generation of a sequence from an HMM by adjusting the parameters. The Baum Welch algorithm and gradient based methods are examples of conventional algorithms that use this criterion for learning. Another example of an optimization criterion that is used to solve the Learning Problem is the Maximum Mutual Information criterion that seeks to train the entire HMM library consecutively.

Other problems that exist with regards to defining and learning HMMs include the Decoding Problem which helps identify the state sequence in an HMM that has the highest probability of generating a sequence of observations O and the Evaluation Problem which helps determine the probability of a particular observation sequence being generated by HMM λ, p(O|λ).

Data on input signals including physiological, non-physiological, and electromagnetic signals is taken and analyzed to reveal sequence and transition of events, beginning with input signal states and the expression of values in each input signal. The training signals for different classes, such as the success or failure in performance of a task or classifying test subject 17 as an expert or novice, are used to train an HMM for each input signal 19 of the class. One embodiment of the present disclosure analyzes the input signals 19 by using the Viterbi algorithm to determine whether an input signal 19 has a high probability of being a success or failure or being generated by an expert or novice.

HMMs provide a fast and accurate technique to develop a comparison to multiple input signals 19. After test subject 17 trains the HMM, it effectively becomes the baseline information against which future coherency of input signals 19 are measured.

Figure 3:
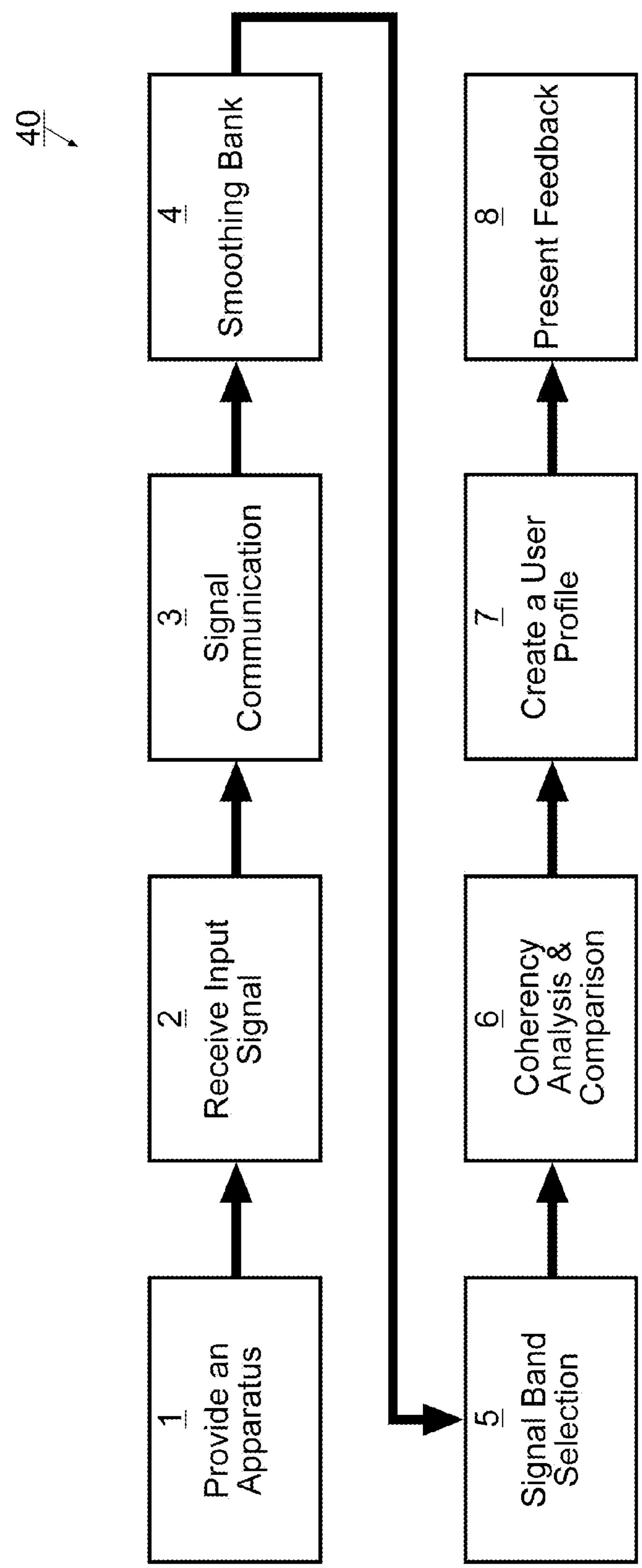
FIG. 3 is a flowchart representing the steps of the method disclosed herein for determining a peak performance state by coherency of input signals from a test subject.

In addition to apparatus 10, the present disclosure also teaches method 40 for determining a peak performance state by coherency of input signals from a test subject. A schematic flow chart of method 40 is displayed in FIG. 3 and includes step 1 providing an apparatus for determining a peak performance state, step 2 receiving input signals from sensors, step 3 communicating the input signals to a processor, and step 4 filtering the input signals through a software smoothing bank. The smoothing bank of step 4 may utilize filtering techniques such as Gaussian smoothing, median filtering, average filtering, butterworth filtering, or any other method of filtering or smoothing known to one of ordinary skill in the art.

After input signals 19 are filtered, method 40 further includes step 5 selecting signals for coherency analysis. The device of apparatus 10 of step 1 includes an exterior sensor that defines a time window in which to collect and analyze input signals. In a given time window, frequency domain representation, smoothed time stream, or any other appropriate technique may be used to perform the coherency analysis.

The next step of method 40 is step 6 coherency analysis and comparison. Apparatus 10 disclosed above includes a number of algorithms for analyzing input signals 19 as a function of a nonlinear relationship and for determining coherency. These algorithms include manifold learning, support vector machine, and the state transition model whose definitions and descriptions are incorporated by reference in method 40. Step coherency analysis and comparison also compares the input signals coherency to baseline data stored in the memory of apparatus 10. This baseline data may be predetermined during the initial implementation of method 40 but thereafter, the baseline can be determined by the Hidden Markov model defined broadly as λ={A,B,Π}. The previous definition and description is also incorporated by reference in method 40.

Following step 6 coherency analysis and comparison, a test subject may create a user profile step 7 utilizing software on the feedback device to provide feedback information step 8 regarding the peak performance states. This information may be assembled by storing a profile for a test subject in the memory of the feedback device based on usage patterns as well as personal preferences. One embodiment of the present disclosure may utilize basic physiological sensing to know the affective and cognitive state of the test subject and contextualize the feedback to the current state of the test subject. For example, galvanic skin sensing and EEG sensing may be input signals selected to generate feedback. In this example, a galvanic skin response and EEG profile will be associated with affective state of the test subject and would allow for adjusting the category of feedback based on the affective state. A contextualized feedback presentation would then be given to the test subject.

Examples of feedback modalities include, but are not limited to audio, video, textual, and haptic feedback. Feedback may be provided through visualizations as well as through a virtual tutor or buddy. This feedback may be delivered by devices such as laptop computer, desktop computers, cell phones, personal data assistants (PDAs), tablet computers, video game consoles, shared large screen displays, smart televisions, or augmented reality displays and programs by way of example. Feedback may also take the form of short messaging service, vibratory motors, force feedback devices, and auditory tones.

A test subject may utilize some or all of these feedback methods in an attempt to train and improve performance of a given activity. Based on the feedback provided in step 8 of method 40, a test subject may engage in mental or physiological exercises such as operant conditioning, mental imagery, or controlled breathing as examples to bring input signal coherence back into the desired peak performance state.

The illustrations and examples provided herein are for explanatory purposes and are not intended to limit the scope of the appended claims.

We claim:

1. A system for determining a peak performance cognitive state of a test subject by coherency of input signals therefrom comprising:

a plurality of sensors, said sensors configured to receive a separate input signal from said test subject during performance of an activity, at least one of said sensors configured to receive cognitive input, a processor, said sensors communicating with said processor, a memory, said memory connected to said processor, an algorithm, said algorithm stored in said memory, and baseline data derived from said test subject during a prior successful completion of the activity and before a comparison with the input signals, said baseline data stored in said memory, whereby said input signals delivered from said sensors to said processor are analyzed by said algorithm as a function of a nonlinear relationship for determining coherency thereof and comparison to said baseline data for predictive determination of the peak performance cognitive state of said test subject before a repeated performance of the activity.

2. The system of claim 1 wherein said algorithm comprises a manifold learning algorithm and a support vector machine algorithm for determining input signal coherency.

3. The system of claim 2 wherein said baseline data is determined by a Hidden Markov model defined as $\lambda=\{A,B,\Pi\}$.

4. The system of claim 1 further comprising a feedback mechanism, said feedback mechanism controlled by said algorithm, for notifying said test subject of the current peak performance state.

5. The system of claim 4 further comprising an exterior sensor, a measurement window, said measurement window defined as a period of time for input signal reception by said sensors, said exterior sensor for determining duration of said measurement window and separate from said sensors for receiving input signals.

6. The system of claim 5 further comprising an additional plurality of sensors for receiving input signals placed proximally the head, heart, and feet of a user.

7. A method for determining a peak performance cognitive state of a test subject by coherency of input signals therefrom during performance of an activity comprising the steps of:

receiving separate input signals by a plurality of sensors, at least one of said sensors configured to receive cognitive input;

communicating the input signals from the sensors to a processor;

analyzing the input signals by the processor with an algorithm as a function of a nonlinear relationship for determining coherency thereof; and comparing the coherency to baseline data derived from the test subject during a prior successful completion of the activity and before a comparison with the input signals and stored in a memory connected to the processor to predictively determine the presence of a peak performance cognitive state in the test subject before a repeated performance of the activity.

8. The method of claim 7 wherein analyzing the input signals with an algorithm further includes the step of providing an algorithm that comprises a manifold learning algorithm and a support vector machine algorithm for determining input signal coherency.

9. The method of claim 8 in which comparing coherency to baseline data further comprises the step of determining baseline data by a Hidden Markov model defined as $\lambda=\{A,B,\Pi\}$.

10. The method of claim 9 wherein receiving input signals from two sensors further includes the step of placing an additional plurality of sensors proximally the head of the user.

11. The method of claim 9 wherein receiving input signals from two sensors further includes the step of placing an additional plurality of sensors proximally the heart of the user.

12. The method of claim 9 wherein receiving input signals from two sensors further includes the step of placing an additional plurality of sensors proximally the feet of the user.

13. The method of claim 9 further comprising the step of providing a feedback mechanism controlled by the algorithm for notifying the test subject of the current peak performance state.

14. The method of claim 13 further including the step of providing an exterior sensor for determining duration of a measurement window defined as a period of time for input signal reception by the sensors.

15. A method for determining a peak performance cognitive state of a test subject by coherency of input signals therefrom comprising the steps of:

providing an apparatus having:

a plurality of sensors, said sensors each for receiving a separate input signal from said test subject during performance of an activity, at least one of said sensors configured to receive cognitive input, a processor, said sensors communicating with said processor, a memory, said memory connected to said processor, an algorithm comprising a manifold learning algorithm and a support vector machine algorithm, said algorithm stored in said memory, baseline data, said baseline data derived solely from the test subject during a prior successful completion of the activity and before a comparison with the input signals and stored in said memory;

receiving separate input signals by the two sensors;

communicating the input signals to the processor;

analyzing the input signals by the processor with the algorithm as a function of a nonlinear relationship for determining predictive coherency thereof; and comparing coherency data to baseline data stored in the memory connected to the processor to determine the presence of a peak performance cognitive state in a test subject before a repeated performance of the activity.

16. The method of claim 15 in which comparing coherency data to baseline data further comprises the step of determining baseline data by a Hidden Markov model defined as $\lambda=\{A,B,\Pi\}$.

17. The method of claim 15 further comprising the step of providing an additional plurality of sensors for receiving input signals placed proximally the head, heart, and feet of the test subject.

18. The method of claim 15 further comprising the step of providing a feedback mechanism, the feedback mechanism controlled by the algorithm, for notifying the test subject of the current peak performance state.

19. The method of claim 18 further including the step of providing an exterior sensor for determining duration of a measurement window defined as a period of time for input signal reception by the sensors.

* * * * *